United States Patent
Long et al.

(10) Patent No.: US 8,657,828 B2
(45) Date of Patent: Feb. 25, 2014

(54) HUMERAL ROTATING BURR GUIDE

(75) Inventors: Jack F Long, Warsaw, IN (US); Stephen R Donnelly, Willoughby, OH (US)

(73) Assignee: Depuy Synthes Products, LLC, Raynham, MA (US)

(*) Notice: Subject to any disclaimer, the term of this patent is extended or adjusted under 35 U.S.C. 154(b) by 113 days.

(21) Appl. No.: 13/348,902

(22) Filed: Jan. 12, 2012

(65) Prior Publication Data

US 2012/0116405 A1  May 10, 2012

Related U.S. Application Data

(62) Division of application No. 12/062,952, filed on Apr. 4, 2008, now Pat. No. 8,114,087.

(51) Int. Cl.
*A61F 5/00* (2006.01)

(52) U.S. Cl.
USPC .......................................................... 606/87

(58) Field of Classification Search
USPC ................. 606/86 R, 87, 88, 89, 96, 98
See application file for complete search history.

(56) References Cited

U.S. PATENT DOCUMENTS

| | | | |
|---|---|---|---|
| 5,779,709 A | 7/1998 | Harris et al. |
| 5,779,710 A | 7/1998 | Matsen |
| 5,961,555 A | 10/1999 | Huebner |
| 6,015,437 A | 1/2000 | Stossel |
| 6,102,953 A | 8/2000 | Huebner |
| 6,168,627 B1 | 1/2001 | Huebner |
| 6,193,758 B1 | 2/2001 | Huebner |
| 6,228,120 B1 | 5/2001 | Leonard et al. |
| 6,530,957 B1 | 3/2003 | Jack |
| 6,620,197 B2 | 9/2003 | Maroney et al. |
| 6,673,114 B2 | 1/2004 | Hartdegen et al. |
| 6,780,190 B2 | 8/2004 | Maroney |
| 7,083,625 B2 | 8/2006 | Berry |
| 7,097,663 B1 | 8/2006 | Nicol et al. |
| 7,229,478 B2 | 6/2007 | Masini |
| 7,297,163 B2 | 11/2007 | Huebner |
| 7,338,496 B2 | 3/2008 | Winslow et al. |
| 7,431,736 B2 | 10/2008 | Maroney et al. |
| 7,517,364 B2 | 4/2009 | Long et al. |
| 2004/0002711 A1 | 1/2004 | Berry |
| 2004/0034431 A1 | 2/2004 | Maroney et al. |
| 2005/0021038 A1 | 1/2005 | Maroney |
| 2006/0036328 A1 | 2/2006 | Parrott et al. |

(Continued)

FOREIGN PATENT DOCUMENTS

| | | |
|---|---|---|
| EP | 0687448 A | 12/1995 |
| EP | 0893098 A2 | 1/1999 |

(Continued)

OTHER PUBLICATIONS

Biomet Orthopedics, Inc., Copeland/Copeland EAS Humeral Resurfacing Head Surgical Technique—2006.

(Continued)

*Primary Examiner* — Sameh Boles (57) ABSTRACT

A cutting guide for removal of bone during arthroplasty. The cutting guide includes a housing having a three-dimensional guide path and an arm coupled to the housing and extending through the guide path. The arm includes a burr. As the arm is slid along the path, the burr simultaneously cuts in two planes on the bone.

6 Claims, 8 Drawing Sheets

(56) References Cited

U.S. PATENT DOCUMENTS

| | | |
|---|---|---|
| 2006/0276903 A1 | 12/2006 | Maroney et al. |
| 2007/0016305 A1 | 1/2007 | Chudik |
| 2007/0027477 A1 | 2/2007 | Chudik |
| 2007/0100353 A1 | 5/2007 | Chudik |
| 2008/0119861 A1 | 5/2008 | Winslow et al. |

FOREIGN PATENT DOCUMENTS

| | | |
|---|---|---|
| EP | 1464305 A2 | 10/2004 |
| FR | 2731897 A1 | 9/1996 |
| FR | 2863859 A | 4/2008 |
| WO | WO 2004/075763 A | 9/2004 |
| WO | WO 2005/016123 A2 | 2/2005 |

OTHER PUBLICATIONS

Depuy, A Johnson & Johnson Company—Global Advantage CTA Humeral Head Design Rationale and Surgical Technique—2000.

European Search Report for Corresponding EPO Application No. 10170055.7-2310 Dated Jan. 10, 2011, 5 Pages.

European Search Report for European Application No. 09157237.0-2310, Dated Aug. 10, 2009, 5 Pages.

HUMERAL ROTATING BURR GUIDE

TECHNICAL FIELD OF THE INVENTION

The present invention relates generally to the field of orthopaedics, and more particularly, to an instrument for use in arthroplasty.

BACKGROUND OF THE INVENTION

Patients who suffer from the pain and immobility caused by osteoarthritis and rheumatoid arthritis have an option of joint replacement surgery. Joint replacement surgery is quite common and enables many individuals to function properly when it would not be otherwise possible to do so. Artificial joints are usually comprised of metal, ceramic and/or plastic components that are fixed to existing bone.

One type of joint replacement surgery is shoulder arthroplasty. During shoulder arthroplasty, the humeral head must be resected to allow for the insertion of a humeral stem into the intramedullary canal of the humerus. The proximal end of the humerus includes the humeral head, which articulates with the glenoid cavity of the shoulder in a ball and socket fashion. The humeral head is nearly hemispherical in form.

The prostheses typically used for shoulder arthroplasty include a stem portion designed to extend into the intramedullary canal of the humerus and a head portion designed to replace the humeral head. The head portion of the prosthesis extends angularly from the stem portion. The resection of the natural humeral head must be made so that the angle of the cut corresponds to the angle between the stem and head portions of the prosthesis. In addition, the rotation of the cut varies to adjust to bone wear or capsulor looseness.

There are eight essential variables relating to humeral arthroplasty. These include: the diameter of curvature of the prosthesis; the percentage of the sphere with this diameter that will be used as prosthetic articular surface; the superior/inferior position of the articular surface relative to the humerus; the anterior/posterior position of the articular surface relative to the humerus; the medial/lateral articular aspect of the articular surface with respect to the humerus; the anterior/posterior angulation (flexion/extension) of the articular surface relative to the prosthesis; the medial/lateral angulation (varus/valgus) of the prosthesis relative to the humerus; and, the rotational alignment of the prosthetic head with respect to the humeral axis. The goal of prosthetic arthroplasty is to duplicate the normal orientation of the humeral articular surface as well as its diameter of curvature and percentage of the sphere.

Many orthopaedic companies currently provide anatomically variable prosthesis with stems that facilitate adjusting the prosthesis to more accurately reflect the anatomy of the individual. For anatomically variable prostheses, most surgical techniques call for a "freehand" cut of the humeral head. Others have rudimentary guides that facilitate a planar cut but only allow for anterior/posterior (version) or medial/lateral adjustment of the cutting plane.

When the humeral head resection is made free hand, the elbow of the patient is flexed to 90° with the patient's forearm aimed at the midline of the operating surgeon's trunk. The humerus is externally rotated to provide the recommended degree of retrotorsion in relation to the axis of elbow motion. The resection is directed away from the surgeon, allowing the surgeon to reproduce the desired retrotorsion in the bone cut. A trial prosthesis may also be placed along the proximal humeral shaft as a guide for the proper inclination of the resection. The possibility for error exists with this free hand approach. Inaccurate resection can result in an ill-fitting prosthesis which may cause complications for the patient and may eventually require replacement of the prosthetic device.

Also, when implanting a proximal humeral resurfacing implant with an extended articulation surface, removal of part or all of the humeral greater tubercle is needed. This removal should allow for proper fitting and fixation of the implant and the extended articulation surface to the resurfaced humeral head and requires cutting in two planes. However, current cutting guides only allow for the cutting of the humeral greater tubercle in one plane at a time. Therefore, the surgeon would need to perform at least two cutting steps (and possibly use two different tools) to properly prepare the humerus. There is a need for a cutting guide that allows for a surgeon to be able to properly remove the humeral greater tubercle in a single step.

SUMMARY OF THE INVENTION

According to one embodiment of the present invention, a cutting guide for removal of bone during arthroplasty is provided. The cutting guide includes a housing having a three-dimensional guide path as well as an arm coupled to the housing. The arm extends through the guide path and includes a burr. As the arm is slid along the path, the burr simultaneously cuts in two planes.

According to another embodiment of the present invention, a method for resecting a portion of a bone in arthroplasty is provided. The method includes providing a housing having a three-dimensional guide path. An arm is placed in the housing, such that the arm is movable along the three-dimensional guide path. The arm is coupled to the burr. The method also includes simultaneously resecting a portion of the bone in a plurality of planes with the burr.

According to yet another embodiment of the present invention, a cutting guide for cutting a form of a head of a bone during arthroplasty is provided. The cutting guide includes a housing adapted to be placed on the head of the bone and an arm rotatably coupled to the housing. A burr is coupled to the arm such that the burr is adapted to cut the from of the bone as the arm rotates about the housing.

BRIEF DESCRIPTION OF THE DRAWINGS

For a more complete understanding of the present invention and the advantages thereof, reference is now made to the following description taken in connection with the accompanying drawings, in which.

DETAILED DESCRIPTION OF THE INVENTION

Embodiments of the present invention and the advantages thereof are best understood by referring to the following descriptions and drawings, wherein like numerals are used for like and corresponding parts of the drawings.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 1:
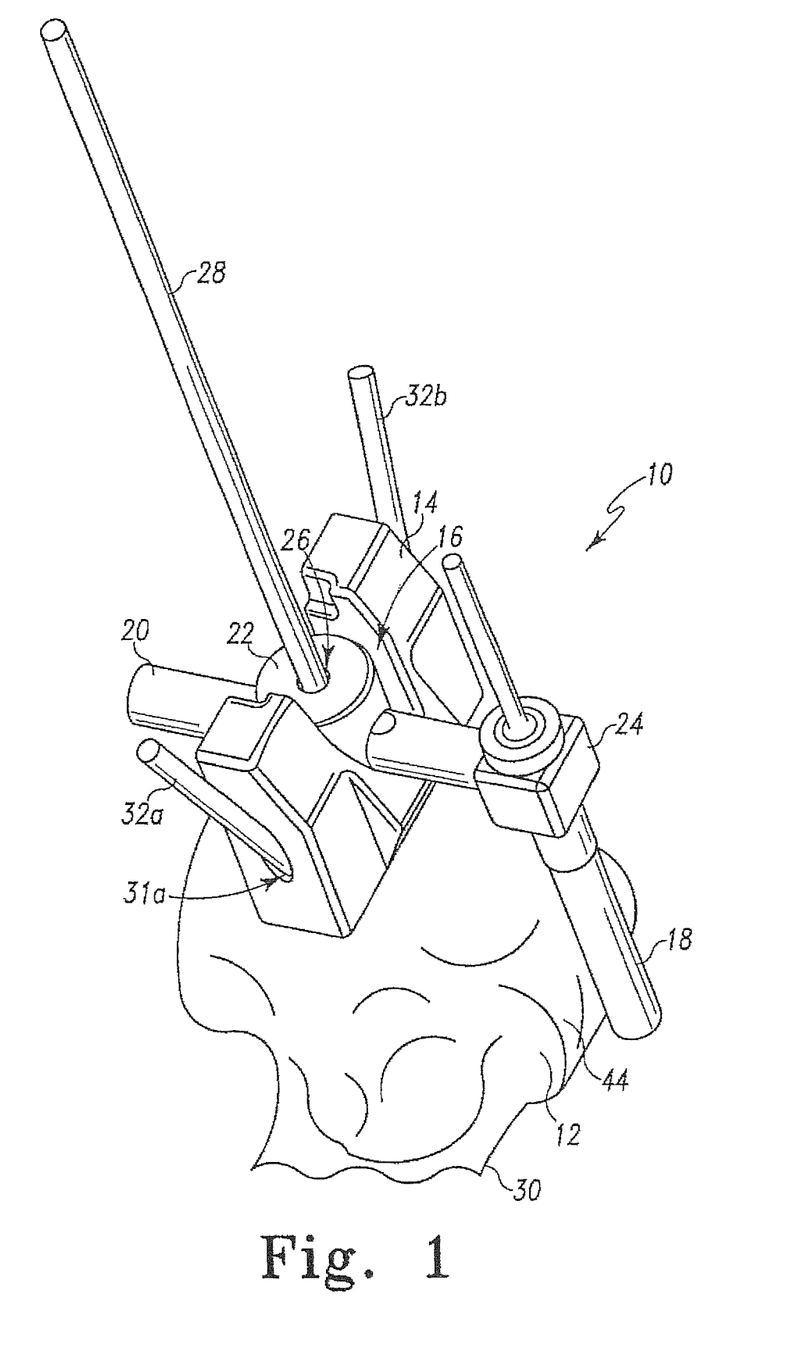
FIG. 1 is a perspective view of a humeral cutting guide on a humerus.
Figure 2:
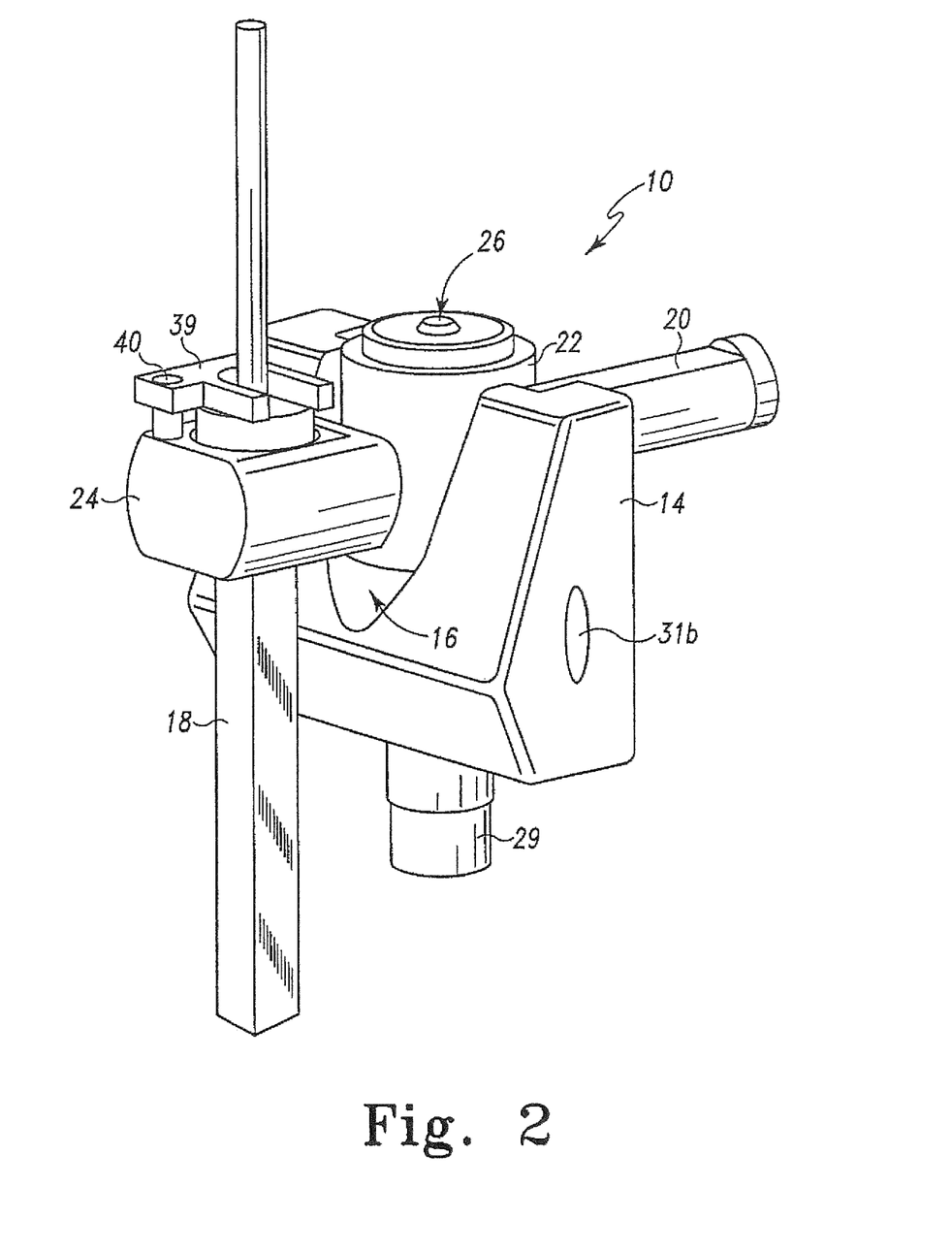
FIG. 2 is a perspective view of the humeral cutting guide of FIG. 1.

Referring now to FIGS. 1 and 2, a cutting guide 10 is provided that allows for the cutting of a humeral head 12. The cutting guide 10 is used to remove a portion of the humeral head 12 to allow for the placement of an implant (not shown). The cutting guide 10 includes a housing 14. The housing 14 includes a three-dimensional guide path, such as a slanted parabolic slot 16 for coupling to a burr 18. The slot 16 extends longitudinally and laterally. The slot 16 defines the path that the burr 18 will cut. The multi-directional nature of the slot 16 enables the burr 18 to move both in the proximal/distal plane and also the medial/lateral plane—thereby allowing for a multiplanar cut.

An arm 20 extends through the slot 16 and includes a burr-attachment end and a quick-connect end. The burr-attachment end is coupled to the burr 18. The arm 20 is held in place in the slot 16 by an adjustable cylinder 22. The arm 20 includes a burr restraint portion 24 that is used to hold the burr 18 on its path. The adjustable cylinder 22 allows the surgeon to adjust the distance between the burr 18 and the housing 14, which will be described in more detail in reference to FIG. 3 below. The quick-connect end 20b of the arm 20 allows the surgeon to hold the burr with one hand while holding a drill portion with the other hand.

The adjustable cylinder 22 includes an opening 26 that extends longitudinally through the adjustable cylinder 22. The opening 26 is adapted to receive a guide pin 28. As shown in FIG. 1, the guide pin 28 extends through opening 26 and a post 29 of the housing 14 into a humerus 30 for holding the cutting guide 10 in place relative to the humeral head 12.

The housing 14 also includes a pair of pin holes 31a, 31b on the sides to align the housing anteriorly and posteriorly on the humeral head 12. Pins 32a, 32b fit through the pin holes 31a, 31b to further affix the housing 14 to the humeral head 12. The pins 32a, 32b prevent the cutting guide 10 from sliding around on the humeral head 12.

Figure 3:
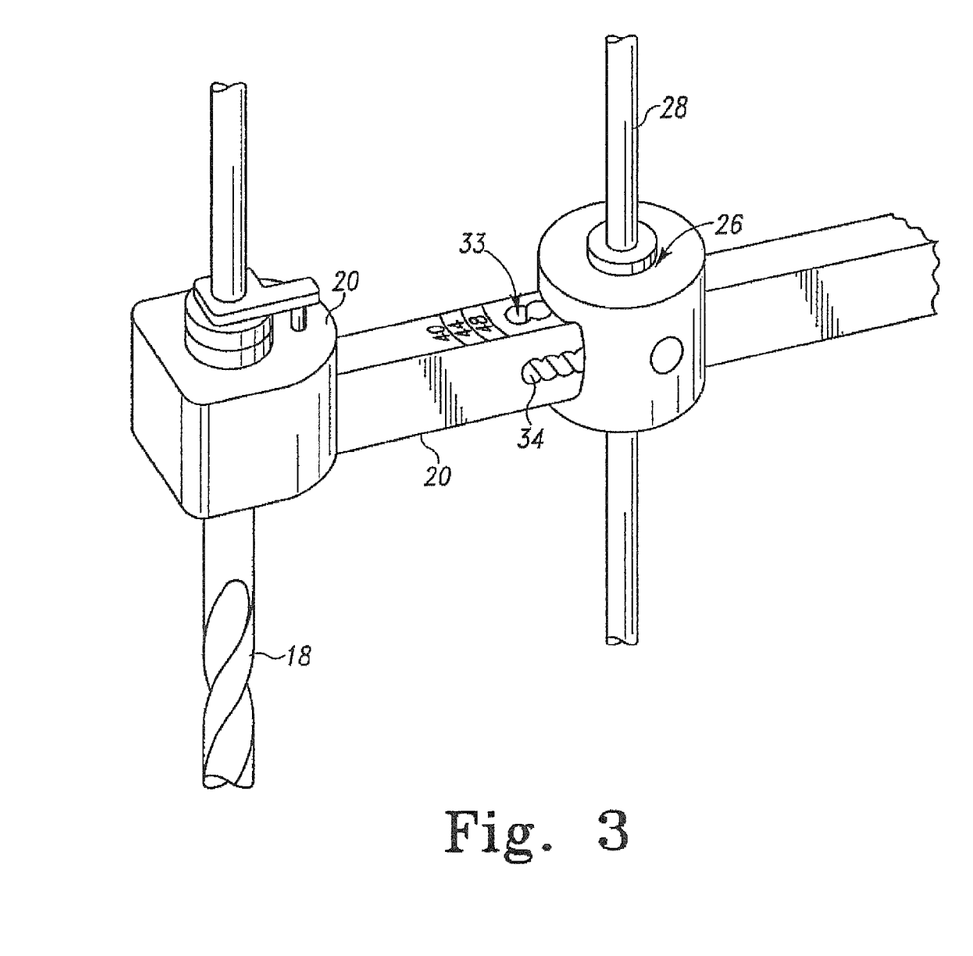
FIG. 3 is a perspective view of a portion of FIG. 2.
Figure 3A:
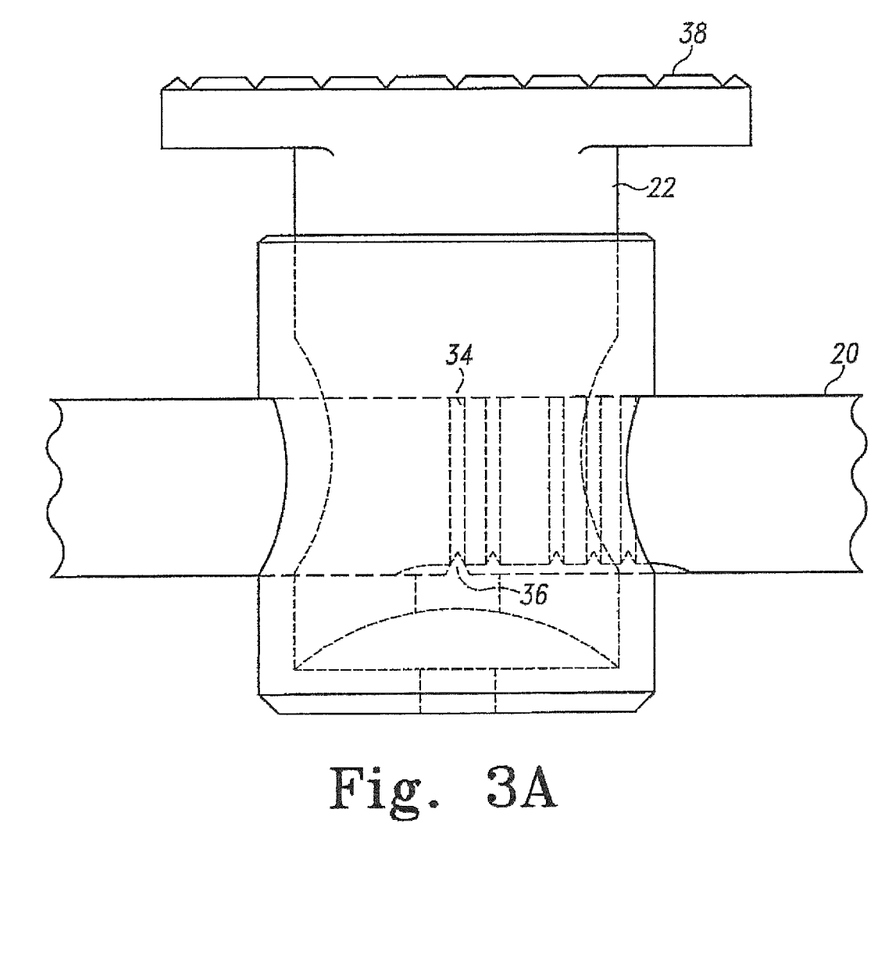
FIG. 3A is a partially see-through view of a portion of the humeral cutting guide of FIG. 1.

Turning now to FIG. 3, a perspective view of the arm 20 is shown. An elongated slot 33 extends through the arm 20. The elongated slot 33 is dimensioned so as to receive the guide pin 28. The arm 20 also includes a plurality of notches 34 that are adapted to correspond with an adjustable pin (not shown). In the embodiment shown in FIG. 3A, the notches 34 extend around the arm 20 and engage a movable ridge 36 on the inside of the adjustable cylinder 22 (FIG. 3A). The ridge 36 couples with one of the notches 34, locking the arm 20 in a particular location relative to the housing 14. A button 38 is included on the top of the adjustable cylinder 22. As best shown in FIG. 3A, when the button 38 is pressed, the ridge 36 disengages the notch 34 so the user can slide the arm 20. In some embodiments of the present invention, the arm 20 may include markings to aid the surgeon in measuring the distance between the cylinder 22 and the burr 18, which will adjust the radius of the cut area.

In an alternative embodiment, the cylinder 22 may include a notch and the arm 20 may include ridges. In other embodiments, other known releasable locking mechanisms may be used.

Returning now to FIG. 2, the restraint portion 24 includes a positioning member 39. The positioning member 39 allows the user to adjust the burr 18 up or down. By being able to adjust the vertical location of the burr 18, the user can control the depth that the burr 18 will cut. The vertically adjustable piece 39 includes a screw 40 that can be adjusted to different heights, allowing the burr 18 to be adjusted.

In another embodiment, the burr 18 may not be vertically adjustable. Instead, there may be provided a plurality of burrs that have different depths, which would allow for different heights to be cut.

Figure 4A:
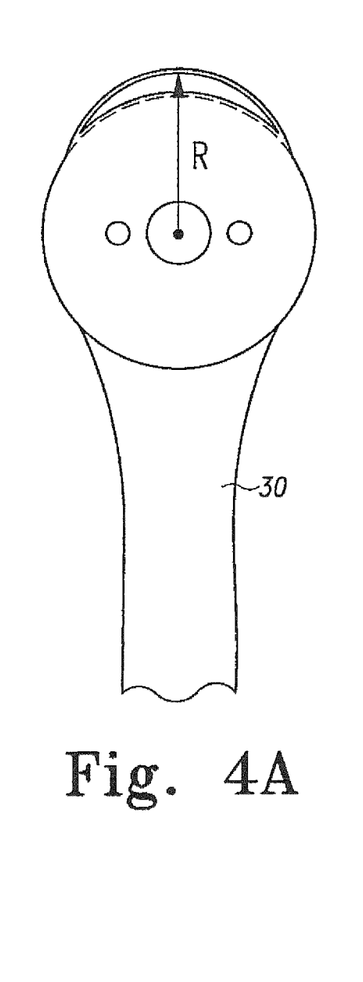
FIG. 4A is a medial-lateral view of a resurfaced humeral head.
Figure 4B:
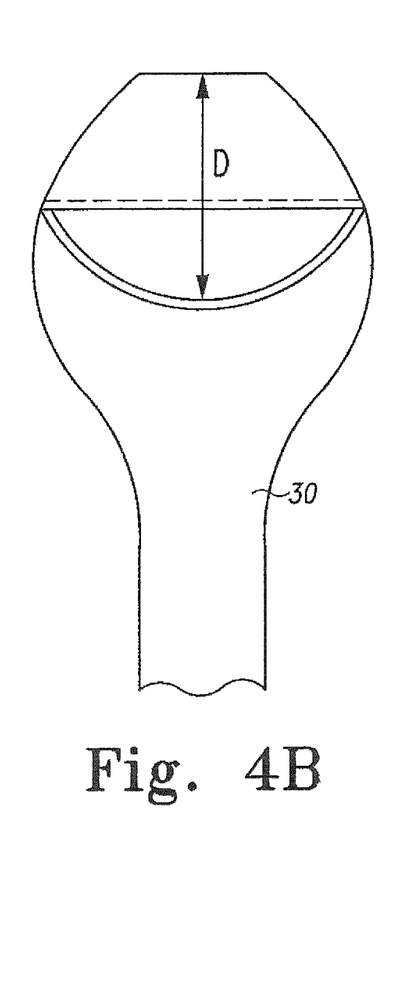
FIG. 4B is a lateral-medial view of a resurfaced humeral head.

FIGS. 4A and 4B show a top and a side view of the humerus 30. As illustrated, the humerus 30 includes a greater humeral tubercle 44 (best seen in FIG. 1) that needs to be either partially or wholly removed. The greater humeral tubercle 44 includes a radius R and a depth D. The cutting guide 10 of the present invention will be able to cut both the radius R and the depth D in a single step, as will be described below.

Figure 5:
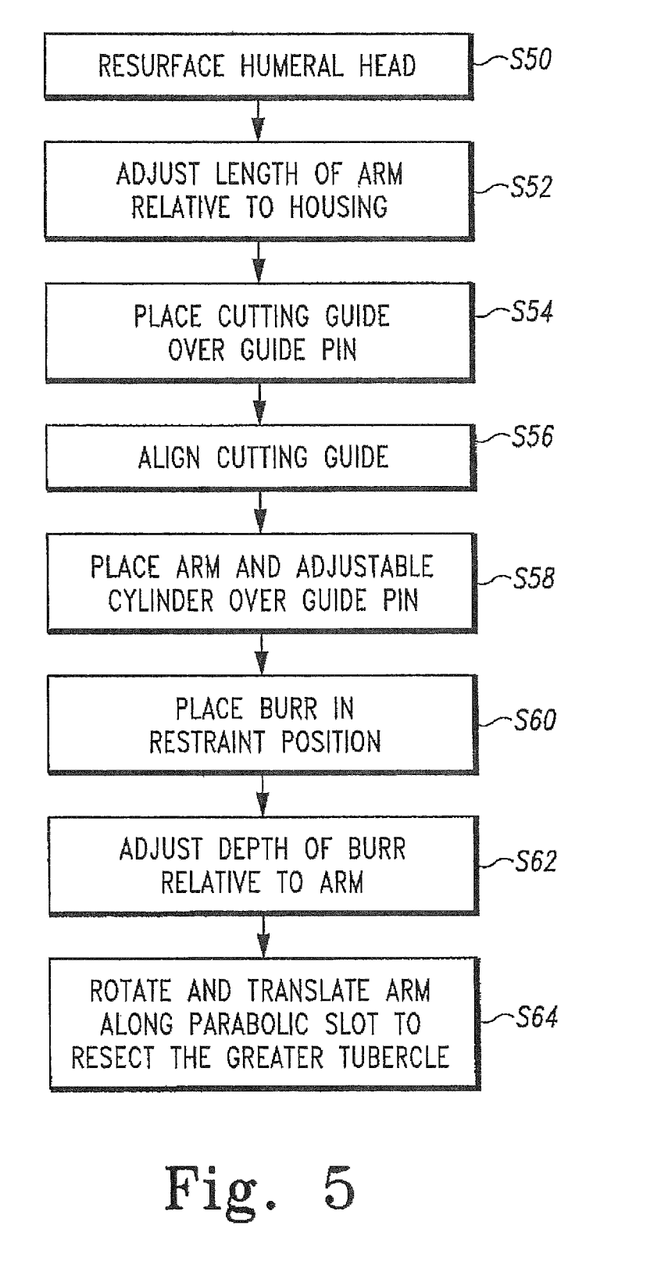
FIG. 5 is a flow chart describing the operation of the humeral cutting guide.

Turning now to FIG. 5, a method for using the cutting guide 10 will be described. First, at step s50, a humeral head 12 is resurfaced using a spherical reamer over the guide pin 28. The reamer allows for a flat surface to be created on the top of the humeral head 12. At step s52, the length of the arm 20 is adjusted to the desired length. Next, at step s54, the cutting guide 10 is placed over the guide pin 28. The housing 14 of the cutting guide 10 sits on the flat on the top of the humeral head 12. The post 29 fits into the reamed hole. Next, at step s56, the cutting guide 10 is aligned using the pin holes 31a, 31b on the housing 14. Pins 32a, 32b are placed in the pin holes 31a, 31b at step s56 to prevent rotation of the housing 14. At step s58, the arm 20 and adjustable cylinder 22 are then placed over the guide pin 28 in the parabolic slot 16 of the housing 20. The burr 18 is then placed into the restraint portion 24 of the arm 20 at step s60. At step s62, the depth of the burr 18 will be adjusted (if so desired). The arm 20 is then rotated and translated along the parabolic slot 16 to resect the radius R and depth D simultaneously on the humerus 30 at step s64. After the required part of the greater tubercle 42 is removed, the cutting guide 10 is then removed from the guide pin 28 and the trialing and implantation of the prosthesis can occur.

In some embodiments, step s52 may take place after the arm 20 is placed over the guide pin 28. In some embodiments, step 62 may not be included. In those embodiments, multiple burrs of different sizes may be included and the surgeon selects one of the burrs depending on the depth the surgeon would like to cut.

By placing the cutting guide 10 on the guide pin 28 that is used in other cutting procedures, reproducible and properly placed cuts can be more easily achieved. Also, because of the three-dimensional parabolic nature of the slot 16, the radius and the depth can be cut simultaneously, allowing for resection in multiple planes. Also, in some embodiments both the arm 20 and the burr are adjustable relative to the housing 14, both the radius and the depth to be cut can be adjusted depending upon the anatomy of the patient or the need of the surgeon.

Figure 6:
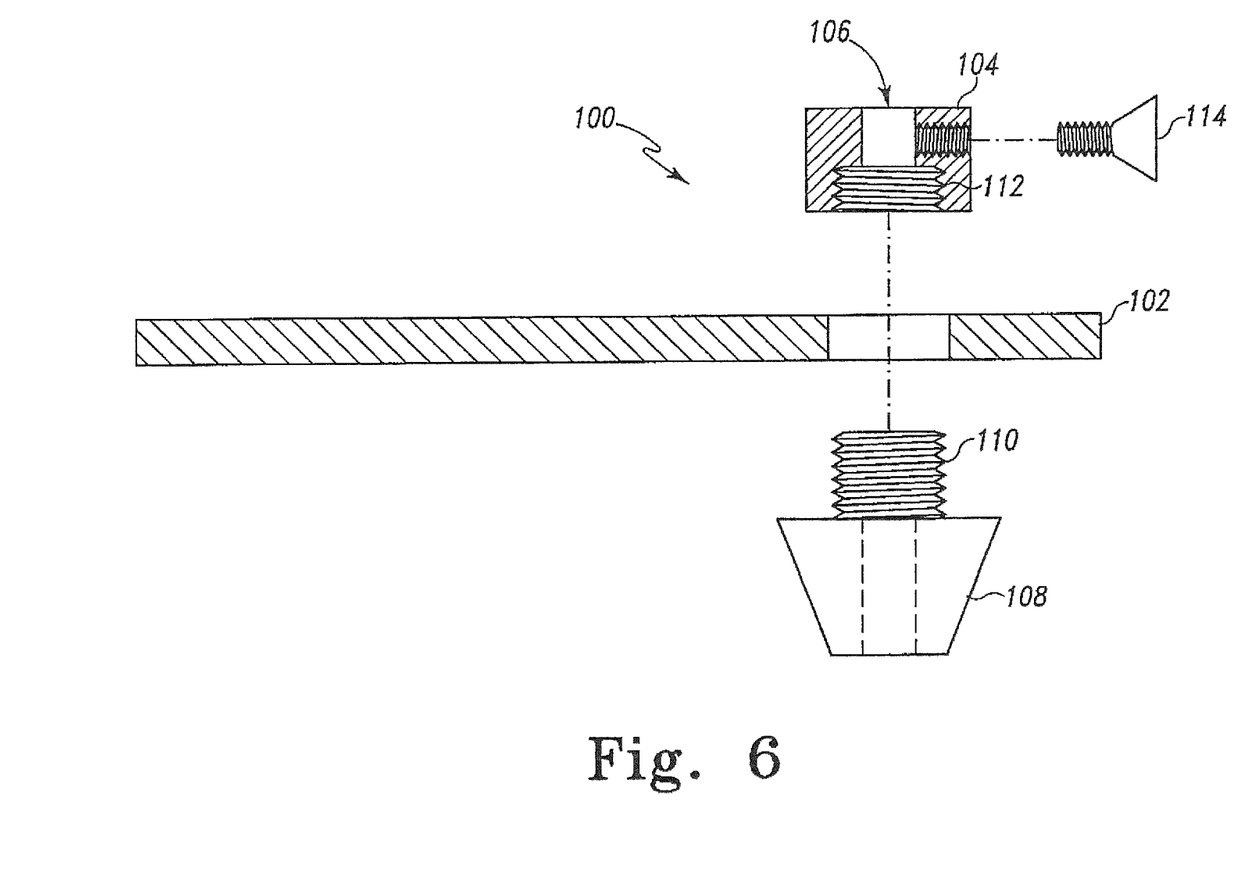
FIG. 6 is perspective view of an alternative embodiment of the present invention.
Figure 7:
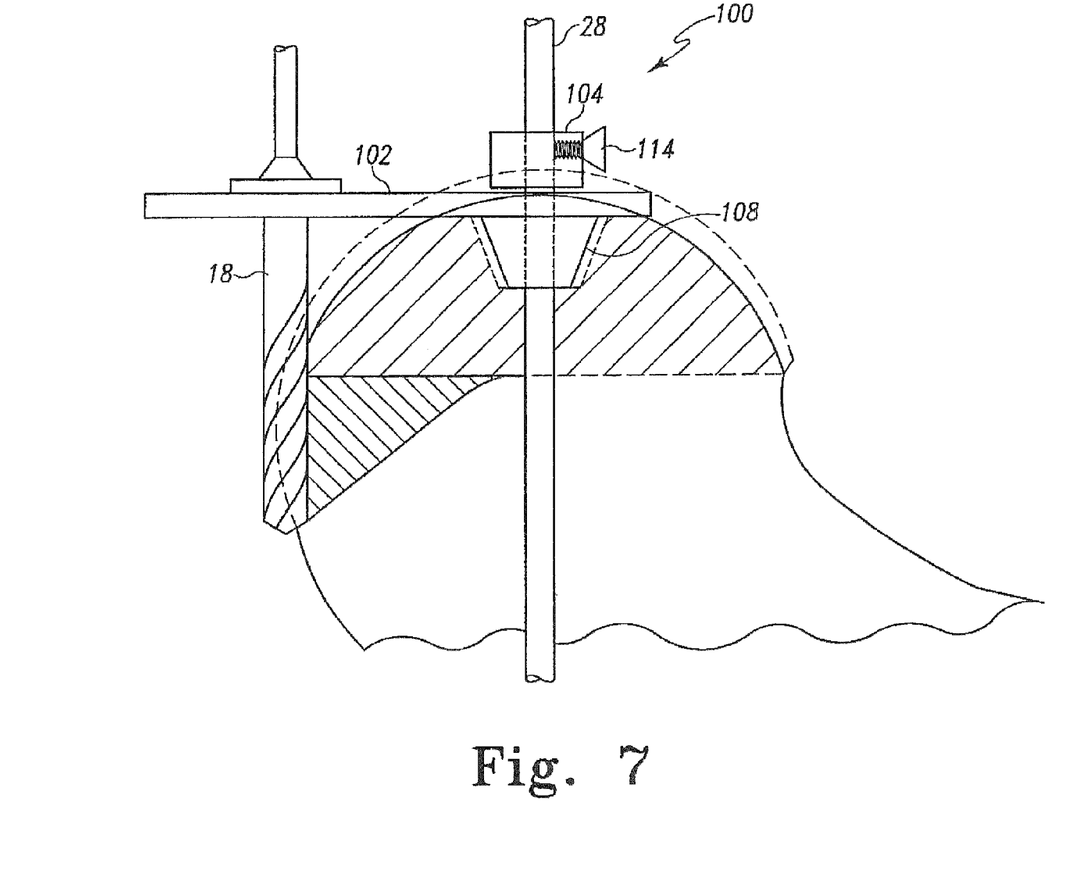
FIG. 7 is an exploded view of the embodiment shown in FIG. 6.

Turning now to FIGS. 6 and 7, another embodiment of the present invention will be described. A cutting guide 100 is provided that includes an arm 102 that couples to the burr 18. The cutting guide 100 further includes a housing 104. The housing 104 includes an opening 106 to enable the housing 104 to slide over the guide pin 28. The cutting guide 100 also includes a stem hole stabilizer 108 that attaches to the housing 104 via a threaded portion 110 as shown in FIG. 6. The threaded portion 110 engages a threaded opening 112 in the housing 104. The housing 104 and stem hole stabilizer 108 can be adjusted vertically relative to the guide pin 28 via a screw 114 that locks the housing in position on the guide pin 28.

In use, the arm 102 swings along a curved path on the humeral head 12, guiding the burr 18. The swinging of the arm 102 causes the burr 18 to cut off a radius of the greater tubercle. In other words, the burr 18 swings along an arcuate path on the greater tubercle. In this embodiment, another cutting guide would need to be used to cut the appropriate depth.

In one embodiment, the burr 18 is made of a stainless steel having a hardness between about 40 and 55 on the Rockwell scale. In embodiments where the burr 18 is only intended to be used once, the burr may be made of a softer metal. In other embodiments, the burr 18 may be made of a softer metal, but may be coated with stainless steel having the hardness described above. The arm 20 may be made of stainless steel or other sterilizable metals. The arm 20 itself may also be a one-time instrument made of a polymer material. The housing 14 may also be made of stainless steel or other sterilizable metal. In other embodiments, the housing may also be made of a polymer material. In the above-described invention, the path cut was an arcuate path that included both a radius and a depth. In other embodiments, the multi-dimensional guide path could be designed so as to cut other dimensions that result in two planes being simultaneously cut. For example, in some embodiments, the path may be a parabolic slot that cuts both a radius and a width. In other embodiments, the path may be of a different shape that cuts an oval or a rectangle while simultaneously cutting another dimension.

Although the above-embodiments have been described being used with a humeral head, it should be understood that the cutting guide of the present invention may be used to cut other bones in preparation of arthroplasty.

Although the present invention and its advantages have been described in detail, it should be understood that various changes, substitutions, and alterations can be made therein without departing from the spirit and scope of the present invention as defined by the appended claims.

We claim:

1. A method for resecting a portion of a bone in arthroplasty, the method comprising: providing a housing having a three-dimensional guide path; placing the housing on head of the bone; placing an arm in the housing such that it is movable along the three-dimensional guide path, wherein an adjustable cylinder couples the arm to the housing within the guide path, and wherein the adjustable cylinder includes a locking mechanism for releasably locking the adjustable cylinder to the arm; coupling a burr to the arm, wherein the arm further includes a restraint portion for coupling the burr to the arm, the restraint portion includes a vertically adjustable piece for adjusting depth of the burr relative to the arm; and simultaneously resecting a portion of the bone in a plurality of planes with the burr as the arm is moved along the three-dimensional guide path.

2. The method of claim 1, wherein the step of using the burr comprises resecting both a radius of a head of the bone and a depth of the head of the bone.

3. The method of claim 1, further comprising, prior to resecting the portion of the bone, adjusting the arm relative to the housing, wherein the adjusting adjusts a radius that will be resected.

4. The method of claim 3, further comprising locking the arm in the adjusted position relative to the housing.

5. The method of claim 1, further comprising, prior to resecting the portion of the bone, adjusting the burr relative to the arm wherein the adjusting adjusts a depth that will be resected.

6. The method of claim 5, further comprising locking the arm in the adjusted position relative to the housing.

* * * * *